United States Patent
Tezuka et al.

(10) Patent No.: US 9,561,172 B2
(45) Date of Patent: *Feb. 7, 2017

(54) COSMETIC COMPOSITION HAVING BOTH TRANSPARENT APPEARANCE AND STRUCTURAL RECOVERABILITY

(75) Inventors: Yoji Tezuka, Kawasaki (JP); Muneaki Iizuka, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 28 days.

This patent is subject to a terminal disclaimer.

(21) Appl. No.: 14/131,769

(22) PCT Filed: Jul. 6, 2012

(86) PCT No.: PCT/JP2012/067397
§ 371 (c)(1),
(2), (4) Date: Jan. 9, 2014

(87) PCT Pub. No.: WO2013/008762
PCT Pub. Date: Jan. 17, 2013

(65) Prior Publication Data
US 2014/0155353 A1  Jun. 5, 2014

(30) Foreign Application Priority Data
Jul. 11, 2011 (JP) ................. 2011-152689

(51) Int. Cl.
*A61K 31/74* (2006.01)
*A61K 8/72* (2006.01)
(Continued)

(52) U.S. Cl.
CPC . *A61K 8/92* (2013.01); *A61K 8/31* (2013.01); *A61K 8/37* (2013.01); *A61K 8/39* (2013.01);
(Continued)

(58) Field of Classification Search
CPC .............. A61K 8/37; A61K 8/39; A61K 8/86;
A61K 8/92; A61K 8/97; A61K
8/31; A61K 8/90; A61K 2800/262; A61Q
19/00; A61Q 5/00
See application file for complete search history.

(56) References Cited

U.S. PATENT DOCUMENTS

2004/0229984 A1  11/2004  Yamato et al.
2006/0189734 A1*  8/2006  Gota ...................... C08L 71/02
524/379
(Continued)

FOREIGN PATENT DOCUMENTS

CN   101052371 A   10/2007
JP   20023340 A    1/2002
(Continued)

OTHER PUBLICATIONS

JP 2006-0282539 A, machine translation (Apr. 7, 2015) plus manual translation of tables (Apr. 2015), 18 pages.*
(Continued)

*Primary Examiner* — Anna Pagonakis
*Assistant Examiner* — Miriam A Levin
(74) *Attorney, Agent, or Firm* — Sughrue Mion, PLLC

(57) ABSTRACT

Provided is a cosmetic composition which has a structure-recovering property, is transparent, is satisfactory in smoothness when applied to the skin or hair, and has a good feeling in use, which comprises components (A) to (D) as described.

8 Claims, 2 Drawing Sheets

(51) Int. Cl.

| | | |
|---|---|---|
| *A61Q 5/00* | (2006.01) | |
| *A61K 8/92* | (2006.01) | |
| *A61K 8/37* | (2006.01) | |
| *A61K 8/39* | (2006.01) | |
| *A61Q 19/00* | (2006.01) | |
| *A61K 8/86* | (2006.01) | |
| *A61K 8/90* | (2006.01) | |
| *A61K 8/97* | (2006.01) | |
| *A61K 8/31* | (2006.01) | |

(52) U.S. Cl.
CPC . *A61K 8/86* (2013.01); *A61K 8/90* (2013.01); *A61K 8/97* (2013.01); *A61Q 5/00* (2013.01); *A61Q 19/00* (2013.01); *A61K 2800/262* (2013.01)

(56) References Cited

U.S. PATENT DOCUMENTS

| | | |
|---|---|---|
| 2007/0280897 A1 | 12/2007 | Maruyama et al. |
| 2009/0163616 A1* | 6/2009 | Ishikubo et al. ............. 523/105 |
| 2010/0190864 A1 | 7/2010 | Ohmori et al. |
| 2014/0142203 A1 | 5/2014 | Texuka et al. |

FOREIGN PATENT DOCUMENTS

| | | | |
|---|---|---|---|
| JP | 2002316971 A | | 10/2002 |
| JP | 2006082539 A | * | 3/2006 ............. B41M 5/00 |
| JP | 2006-282539 A | | 10/2006 |
| JP | 2006282540 A | | 10/2006 |
| JP | 2007217392 A | | 8/2007 |
| JP | 2007269719 A | | 10/2007 |
| JP | 200819239 A | | 1/2008 |
| JP | 200888127 A | | 4/2008 |
| JP | 2008-188557 A | | 8/2008 |
| JP | 2008-239496 A | | 10/2008 |
| JP | 2009-108261 A | | 5/2009 |
| JP | 2010-24159 A | | 2/2010 |
| JP | 2010024159 A | * | 2/2010 ............... A61K 8/86 |
| JP | 2010179277 A | * | 8/2010 ............. B01D 19/04 |
| JP | 201217305 A | | 1/2012 |
| WO | 2006038724 A1 | | 4/2006 |

OTHER PUBLICATIONS

JP 2010-024259 A, machine translation (Apr. 7, 2015), 36 pages.*
JP 2010-179277 A, machine translation (Apr. 16, 2016), 40 pages.*
Clariant, Process aids for the Chemical Industry: Surfactants (2009), 27 pages.*
Kansas University, HLB Values of Some Surfactants, [Downloaded from internet <URL: http://pskills.pharm.ku.edu/phar520/dosageforms/Emulsions/lecture/HLBTables.pdf >], [Retrieved Apr. 15, 2016], 2 pages.*
Kao Chemicals, Polyoxyethylene castor oils, [Retrieved from internet <URL: http://chemical.kao.com/us/products/class/c020505.html >], [Downloaded Apr. 15, 2016], 1 page.*
Salimon et al., Fatty Acid Composition and Physicochemical Properties of Malaysian Castor Bean *Ricinus communis* L. Seed Oil, Sains Malaysiana (2010), 39 (5): 761-764, total 4 pages.*
University of North Carolina, The Pharmaceutics and Compounding Laboratory, Emulsions: Preparation and Stabilization, Commonly Used Emulsifiers and Their HLB Values, [Downloaded from internet <URL: http://pharmlabs.unc.edu/labs/emulsions/hlb.htm >], [Retrieved Apr. 15, 2016], 2 pages.*
Extended European Search Report dated Feb. 20, 2015 issued by European Patent Office in counterpart European Patent Application No. 12811817.1, 7 pages.
Office Action dated Dec. 3, 2014 issued by The State Intellectual Property Office of The People's Republic of China in counterpart Chinese Patent Application No. 201280034759.0, 11 pages.
International Search Report, dated Oct. 9, 2012, issued by the International Searching Authority in counterpart International Application No. PCT/JP2012/067397 , 5 pages.
English Translation of Written Opinion, dated Oct. 9, 2012, issued by the International Searching Authority in counterpart International Application No. PCT/JP2012/067397.
Office Action dated Feb. 29, 2016, issued by the Japanese Intellectual Property Office in counterpart Japanese Application in 2012-152030.

* cited by examiner

COSMETIC COMPOSITION HAVING BOTH TRANSPARENT APPEARANCE AND STRUCTURAL RECOVERABILITY

TECHNICAL FIELD

The present invention relates to a cosmetic composition containing a polyalkylene glycol derivative.

BACKGROUND ART

For cosmetics, in order to impart smoothness and a moist feeling to the skin and hair, oily agents, e.g., hydrocarbon oils such as liquid paraffin and squalane, oils and fats and triglycerides represented by vegetable oils, ester oils having an ester linkage, silicone oils such as dimethylsiloxane, and the like are employed. In particular, oily agents that are transparent liquids and have a low viscosity at ordinary temperature have been frequently used owing to a good feeling.

Examples of transparent cosmetics highly blended with an oily agent may include cleansing oils, hair oils, massage oils, and the like. An excellent structure-recovering property may be mentioned as a consumer's need for these cosmetics in recent years.

The structure-recovering property is a property that viscosity decreases by the action of an external force but returns to the original one when the external force is suppressed. In general, a low-viscosity oily agent causes liquid dripping when taken in the hand, and thus it is difficult to apply it to a suitable part of the skin in a proper quantity. Therefore, it is required to have a high viscosity at the time when it is taken out of a vessel or before it is applied to the skin. On the other hand, at the time when it is applied (an external force is imparted), it is required not to impair the smoothness intrinsic to the oily agent. That is, when a feeling in use is good and the structure-recovering property is exhibited, added value of commercial products can be enhanced.

In order to impart the structure-recovering property, it is common to add a gelling agent or thickening agent (hereinafter referred to as gelling agent) to control the viscosity, but it is technically difficult to obtain a transparent gel in an oily system. As the reasons, there are mentioned the fact that the oily agent includes various chemical substances such as hydrocarbon oils, vegetable oils and triglycerides, ester oils, and silicone oils and thus there are many kinds of media and the fact that it is difficult to form an association by the action of electric charge since electric conductivity is poor unlike the case in an aqueous system. Therefore, in order to control viscosity in an oily system, it is common to utilize aggregation induced by a gelling agent or a crystal structure, so that it is difficult to obtain a transparent cosmetic composition and there has not been obtained a cosmetic composition which satisfies a feeling in use at the time when it is applied to the skin or hair.

Namely, it has been desired to develop a cosmetic composition which has the structure-recovering property, is transparent, and exhibits a good feeling in use, with containing a large amount of an oily agent.

In order to enhance the viscosity of the oily agent, some gelling agents have been hitherto proposed and oily gelling agents having a hydrogen bond part such as a hydroxyl group or an amide group have been developed. For example, a technology using 12-hydroxystearic acid and a dextrin fatty acid such as dextrin palmitate (Patent Document 1), an N-acylamino acid derivative such as N-2-ethylhexanoyl-L-glutamic acid dibutylamide (Patent Document 2), and the like have been proposed. They have a thickening mechanism dependent on a hydrogen bond which strongly interacts even in an oil and exhibit a gelling effect in a small amount, but they are not suitable for use in preparations which particularly require the structure-recovering property.

Moreover, a gel composition containing a specific polyoxyalkylene ether that is a block-type alkylene oxide derivative and an oily agent and water has been also proposed (Patent Document 3). The composition has a gel-forming ability having an excellent structure-recovering property (thixotropic property) and a transparent feeling, but there is a further room for improvement in a feeling in use, for example, a feeling when applied and spreadability.

PRIOR ART DOCUMENTS

Patent Documents

Patent Document 1: JP-A-2002-3340
Patent Document 2: JP-A-2002-316971
Patent Document 3: JP-A-2008-19239

SUMMARY OF THE INVENTION

Problems that the Invention is to Solve

A problem that the invention is to solve is to provide a cosmetic composition which has a structure-recovering property, is transparent, and has an extremely good feeling in use, for example, smoothness when applied to the skin or hair, fitness with the skin, and the like.

Means for Solving the Problems

As a result of extensive studies, the present inventors have found that the above problem is solved by blending a specific polyalkylene glycol derivative and a specific nonion surfactant.

Namely, the present invention lies on the following.

(1) A cosmetic composition comprising the following components (A) to (D), wherein the component (A) is from 0.1 to 30% by mass, the component (B) is from 0.1 to 50% by mass, the component (C) is from 50 to 95% by mass, and the component (D) is from 0.01 to 10% by mass, and the mass ratio of the component (A) to the component (B), (A)/(B) is from 1/5 to 5/1:

(A) a polyalkylene glycol derivative represented by the following formula (I):

$$Z-\{O-(EO)_a-(AO)_k-H\}_m \qquad (I)$$

wherein Z is a residual group resulting from removal of hydroxyl groups from a polyhydric alcohol having 3 to 6 hydroxyl groups, m is from 3 to 6, EO is an oxyethylene group, AO is an oxyalkylene group having 4 to 8 carbon atoms, and EO and AO are bonded in a block form;

a represents an average addition mole number of EO and k represents an average addition mole number of AO, and a is from 1 to 50 and k is from 1 to 50; and the mass ratio of EO is from 10 to 75 parts by mass relative to 100 parts by mass of the total amount of EO and AO, (B) a nonionic surfactant having a polyoxyethylene group and a hydrocarbon group having 12 to 22 carbon atoms and exhibiting an HLB of 8 to 14, (C) one or two or more oily agents selected from ester oils and triglycerides which are liquid at 25° C., and (D) water.

(2) The cosmetic composition according to (1), wherein a part of the component (C) is replaced by the following component (E) and the amount of the component (C) is 30 parts by mass or more relative to 100 parts by mass of the total amount of the component (C) and the component (E):

(E) one or two or more oily agents selected from hydrocarbon oils and silicone oils which are liquid at 25° C.

(3) The cosmetic composition according to (1) or (2), wherein AO is a 1,2-oxybutylene group.

(4) The cosmetic composition according to any one of (1) to (3), wherein the component (B) is a nonionic surfactant having a branched or unsaturated hydrocarbon group having 12 to 22 carbon atoms.

Advantage of the Invention

The cosmetic composition of the invention can achieve both of a transparent appearance and a structure-recovering property although the composition has a composition containing a large amount of oily components. Also, since the composition has an excellent structure-recovering property, liquid dripping is not observed at the time when it is taken out of a vessel and a proper quantity thereof can be taken in the hand without smearing the vessel. When it is applied to the skin and an external force is imparted, for example, spreading it by a fingertip, the viscosity decreases and a smooth feeling intrinsic to an oily preparation can be obtained, so that a feeling in use, such as fitness with the skin or hair, is also extremely good.

MODE FOR CARRYING OUT THE INVENTION

Figure 1:
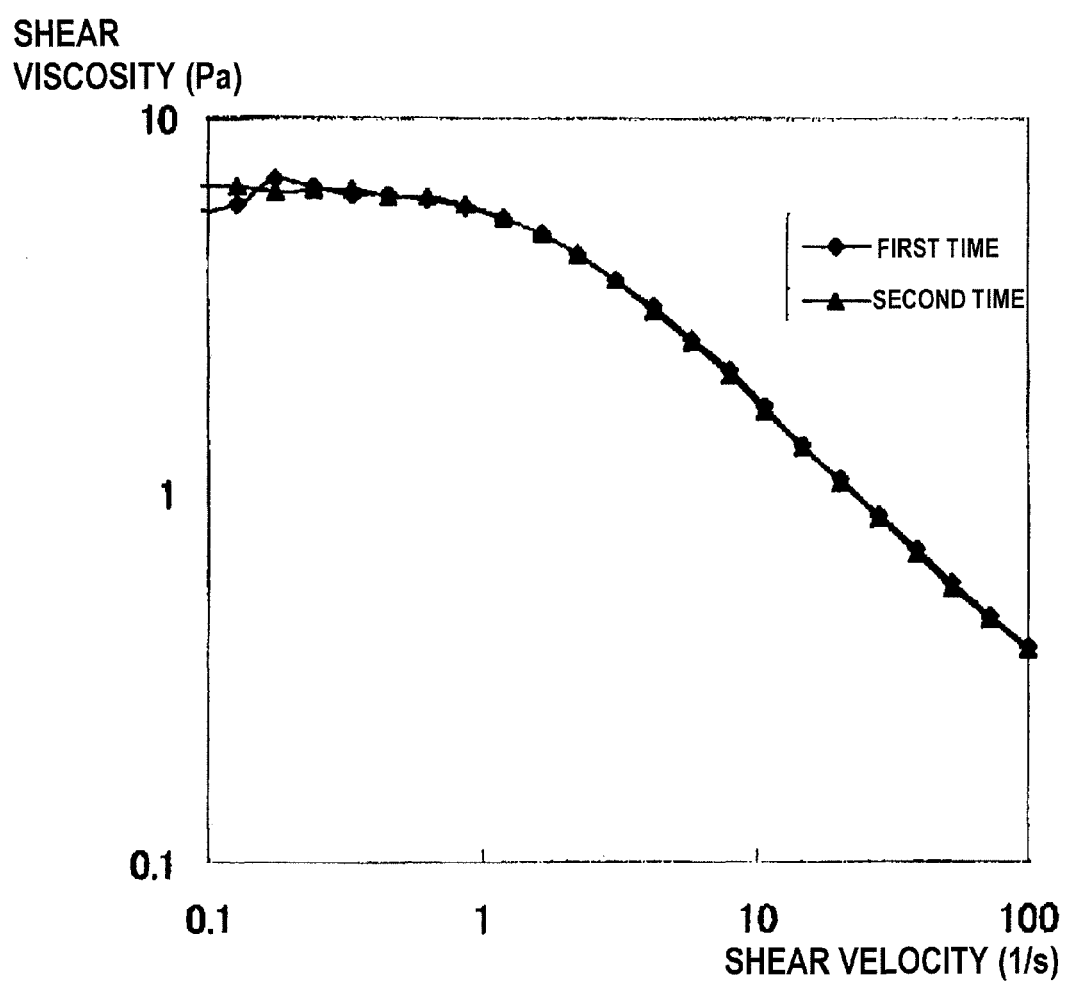
FIG. 1 is a drawing showing a relationship between shear velocity and shear viscosity of the cosmetic composition of Example 13.

The component (A) is a polyalkylene glycol derivative represented by the following formula (I):

$$Z\text{—}\{O\text{-}(EO)_a\text{-}(AO)_k\text{—}H\}_m \qquad (I)$$

wherein Z is a residual group resulting from removal of hydroxyl groups from a polyhydric alcohol having 3 to 6 hydroxyl groups. Examples of the polyhydric alcohol include glycerin and trimethylolpropane having three hydroxyl groups, diglycerin, erythritol, pentaerythritol, sorbitan, and methylglycoside having four hydroxyl groups, xylitol and triglycerin having five hydroxyl groups, and sorbitol, inositol, and dipentaerythritol having six hydroxyl groups. Preferred are residual groups obtained by removing hydroxyl groups from alcohols having four or more hydroxyl groups and, owing to a high gelling ability, more preferred are diglycerin and pentaerythritol having four hydroxyl groups.

m is from 3 to 6, preferably from 4 to 6, more preferably 4. When m is 2 or less or is 7 or more, a sticky feeling is generated at the application and also a smooth feeling in use is not obtained, so that the case is not preferred.

EO is an oxyethylene group, a represents an average addition mole number of EO, and a×m is a total addition mole number of EO in the formula (I). a is from 1 to 50, preferably from 10 to 45. When a is smaller than 1, a sufficient hydrophilicity is not obtained and a cosmetic composition having a structure-recovering property is hardly obtained. Moreover, when a is larger than 50, crystallinity of the EO chain becomes high, so that a transparent cosmetic composition is hardly obtained.

$(EO)_a$ is a polyoxyethylene chain and becomes a hydrophilic group in the polyalkylene glycol derivative of the invention.

AO is an oxyalkylene group having 4 to 8 carbon atoms, and the AO chain becomes a lipophilic group in the polyalkylene glycol derivative of the formula (I). Since the AO chain contributes an improvement in compatibility between the component (A) and the component (C) and/or the component (E), the chain is an essential part for retaining the stability of the cosmetic composition.

In the case where AO has 3 carbon atoms, the compatibility with the oily agent is poor and desired thickening ability is not obtained. Furthermore, in the case where AO has 9 or more carbon atoms, the feeling in use tends to become worse, so that the case is not preferred.

Examples of AO include a 1,2-oxybutylene group having 4 carbon atoms, a 1,2-oxypentylene group having 5 carbon atoms, a 1,2-oxyhexylene group having 6 carbon atoms, a 1,2-oxyheptylene group having 7 carbon atoms, and a 1,2-oxyoctylene group having 8 carbon atoms, but preferred is a 1,2-oxybutylene group or a 1,2-oxyoctylene group and more preferred is a 1,2-oxybutylene group. AO may be one kind or two kinds or more and in the case where it is two kinds or more, the addition form may be any of a random form or a block form.

k represents an average addition mole number of AO, and k×m represents a total average addition mole number of AO in the formula (I). k is from 1 to 50, preferably from 5 to 30. When k is smaller than 1, a sufficient lipophilicity is not obtained and the compatibility between the component (A) and the component (C) and/or the component (E) is poor, so that a stable composition is hardly obtained. Moreover, when k is larger than 50, a sticky feeling is generated, so that there is a case where a feeling in use is poor and hence the case is not preferred.

When the total content of EO and AO is taken as 100 parts by mass, the mass ratio of EO is from 10 to 75 parts by mass. Preferred is from 20 to 75 parts by mass. More preferred is from 30 to 75 parts by mass. When the mass ratio is smaller than 10 parts by mass, a hydrated region decreases and gelation does not take place even when water of the component (D) is added. Moreover, when the mass ratio is larger than 75 parts by mass, the ratio of the EO chain becomes large, so that crystallinity increases and hence a transparent cosmetic composition is not obtained.

EO and AO are bonded in a block form. In a random form, an objective oily cosmetic composition cannot be obtained.

The polyoxyalkylene glycol derivative represented by the formula (I) of the invention can be produced by known methods. For example, the derivative can be obtained by addition polymerization of a polyhydric alcohol having 3 to 6 hydroxyl groups with oxyethylene and an oxyalkylene having 4 to 8 carbon atoms in this order under an alkali or acid catalyst.

The component (A) is blended in an amount of 0.01 to 30% by mass relative to the total mass of the cosmetic composition. The amount is preferably from 0.1 to 20% by mass, more preferably from 1 to 15% by mass. When the amount is less than 0.01% by mass, the desired structure-recovering property is not obtained. When the amount exceeds 30% by mass, a sticky feeling is generated when the composition is applied and thus the case is not preferred.

The component (B) is a nonionic surfactant having a polyoxyethylene chain (EO chain) and a hydrocarbon group having 12 to 22 carbon atoms and exhibiting an HLB of 8 to 14. Incidentally, the nonionic surfactant and polyoxyethylene are sometimes singly referred to as nonion and POE, respectively.

HLB is an abbreviation of Hydrophile-Lipophile Balance and is a concept resulting from numeric conversion of the balance between the hydrophilic group and the lipophilic group of a surfactant. In general, it is represented in the range of 0 to 20 and a higher numerical value shows higher hydrophilicity. HLB can be calculated from the following formula (1) or (2).

POE Alkyl Ether-Type Nonionic Surfactant $$HLB = \text{Mass fraction of oxyethylene group}/5 \quad (1)$$

Polyhydric Alcohol-Fatty Acid Ester-Type Surfactant $$HLB = 20(1 - S/A) \quad (2)$$

S: saponification value of ester, A: acid value of fatty acid (Source: "Shin-pan Kaimen Kasseizai Handobukku (New Edition Surfactant Handbook)" Kougaku Tosho K. K.)

When the length of the EO chain is insufficient and HLB is smaller than 8, the hydration force with water of the component (D) is poor and desired structure-recovering property and transparency are not obtained. From such a viewpoint, HLB is preferably 8.5 or more, most preferably 9.0 or more.

When HLB exceeds 14, hydration with water is strong and the composition tends to coagulate by the influence of the EO chain, so that transparency is not obtained in some cases and hence the case is not preferred.

Examples of the hydrocarbon group having 12 to 22 carbon atoms include a lauryl group, a tridecyl group, a myristyl group, a palmityl group, a cetyl group, an isopalmityl group, a stearyl group, an isostearyl group, an oleyl group, an octyldodecyl group, a vehenyl group, and the like and the hydrocarbon group may be a mixed alkyl group thereof. Of these, from the viewpoints of compatibility and transparency, branched saturated hydrocarbon groups or unsaturated hydrocarbon groups having 12 to 22 carbon atoms are preferred. Particularly preferred as such lipophilic groups are an oleyl group, an isopalmityl group, and an isostearyl group. When the carbon number is smaller than 12, a desired structure-recovering property is not obtained and thus the case is not preferred. Also, when the carbon number exceeds 22, transparency is not obtained.

The component (B) may be any of an ester-type, an ether-type, a linear-type, and a multi-chain-type as long as HLB ranges from 8 to 14. Moreover, the degree of polymerization and the esterification ratio of the oxyethylene group are not particularly limited.

For instance, examples thereof include POE (polyoxyethylene) oleyl ether, POE isopalmityl ether, POE isostearyl ether, POE monooleate, POE monoisostearate, POE dioleate, POE diisostearate, POE sorbitol monooleate, POE sorbitol dioleate, POE sorbitol trioleate, POE sorbitol tetraoleate, POE sorbitol pentaoleate, POE sorbitol hexaoleate, POE sorbitol monoisostearate, POE sorbitol diisostearate, POE sorbitol triisostearate, POE sorbitol tetraisostearate, POE sorbitol pentaisostearate, POE sorbitol hexaisostearate, POE glycerin monooleate, POE glycerin dioleate, POE glycerin trioleate, POE glycerin monoisostearate, POE glycerin diisostearate, POE glycerin triisostearate, POE sorbitan monooleate, POE sorbitan sesquioleate, POE sorbitan trioleate, POE sorbitan monoisostearate, POE sorbitan sesquiisostearate, POE sorbitan triisostearate, and the like.

Of these, for making transparency good, the oily agent is preferably liquid at 25° C. Also, for further strengthening the hydration of the component (D) with water, an ester-type is preferred. Therefore, preferred examples include POE monooleate, POE monoisostearate, POE dioleate, POE diisostearate, POE sorbitol tetraoleate, POE sorbitol tetraisostearate, POE glycerin triisostearate, POE glycerin monoisostearate, POE sorbitan monooleate, POE sorbitan monoisostearate, and the like. For making gelling ability good, a linear type is further preferred. As such nonions, POE monooleate, POE monoisostearate, POE dioleate, and POE diisostearate may be mentioned.

The component (B) is blended in an amount of 0.1 to 50% by mass relative to the total mass of the cosmetic composition. The amount is preferably from 0.1 to 30% by mass, more preferably from 1 to 20% by mass. When the amount is less than 0.1% by mass, the desired structure-recovering property is not obtained. When the amount exceeds 50% by mass, transparency cannot be maintained and a sticky feeling is observed when the composition is applied and thus the case is not preferred. The component (B) may be used with mixing two or more kinds thereof.

The mass ratio of the component (A) to the component (B), (A)/(B) is from 1/5 to 5/1, preferably from 1/3 to 3/1. When the ratio is smaller than 1/5, the structure-recovering property is not obtained and, when the ratio is larger than 5/1, transparency is hardly obtained and thus the cases are not preferred.

The component (C) is one or two or more oily agents selected from ester oils and triglycerides which are liquid at 25° C.

Examples of the ester oils include ethyl oleate, ethyl linoleate, isopropyl myristate, isopropyl palmitate, isopropyl isostearate, cetyl 2-ethylhexanoate, isocetyl 2-ethylhexanoate, stearyl 2-ethylhexanoate, isostearyl 2-ethylhexanoate, cetyl palmitate, 2-ethylhexyl palmitate, 2-hexyldecyl isostearate, isostearyl isostearate, trimethylolpropane triisostearate, myristyl myristate, cetyl myristate, octyldodecyl myristate, isostearyl myristate, isocetyl myristate, hexyl laurate, decyl oleate, octyldodecyl oleate, isostearyl pivalate, isopropyl isostearate, isononyl isononanoate, 2-ethylhexyl isononanoate, isodecyl isononanoate, isotridecyl isononanoate, octyldodecyl erucate, neopentyl glycol didecanoate, pentaerythrityl tetraethylhexanoate, diisostearyl malate, triethylhexanoate trimethylolpropane didecyl adipate, didecyl adipate, cholesteryl isostearate, batyl isostearate, hardened caster oil monohydroxystearate, lanolin fatty acid isostearyl ester, lanolin fatty acid isopropyl ester, lanolin fatty acid octyldodecyl ester, cetyl ricinoleate, dioctyl succinate, cetyl lactate, propylene glycol dicaprylate, propylene glycol dicaprate, propylene glycol dinonanoate, propylene glycol di(caprylate.caprate), propylene glycol diisostearate, propylene glycol dioleate, and the like. One kind or two or more kinds thereof may be used.

Examples of the triglycerides include triglycerides of glycerin with a higher fatty acid having 6 or more carbon atoms, such as caproic acid, caprylic acid, capric acid, 2-ethylhexanoic acid, isotridecanoic acid, isopalmitic acid, isostearic acid, eicosanoic acid, or oleic acid, animal and vegetable oils and fats such as olive oil, sunflower seed oil, safflower oil, castor oil, and camellia oil, and the like.

Preferable ester oils include cetyl 2-ethylhexanoate, isocetyl 2-ethylhexanoate, isopropyl palmitate, 2-ethylhexyl palmitate, isopropyl isostearate, 2-hexyldecyl isostearate, octyldodecyl myristate, isopropyl myristate, isostearyl myristate, isocetyl myristate, isononyl isononanoate, 2-ethylhexyl isononanoate, isodecyl isononanoate, and isotridecyl isononanoate.

Moreover, preferable triglycerides include triglycerides of glycerin with a higher fatty acid having 6 to 10 carbon atoms, such as caproic acid, caprylic acid, capric acid, or 2-ethylhexanoic acid or a mixture thereof, for example, a glyceride of tri(caprate/caprilate).

In the cosmetic composition of the invention, a part of the component (C) can be replaced by the component (E).

The component (E) is one or two or more oily agents selected from hydrocarbon oils and silicone oils which are liquid at 25° C. The hydrocarbon oils include liquid paraffin, hydrogenated polyisobutene, hydrogenated polydecene, squalane, squalene, pristane, light isoparaffin, light liquid isoparaffin, heavy liquid isoparaffin, liquid isoparaffin, tetradecene, isohexadecane, isododecane, α-olefin oligomers, and the like. Preferred are liquid paraffin, hydrogenated polyisobutene, and squalane. The silicone oils include dimethicone, cyclomethicone, phenyldimethicone, and the like, but preferred is cyclomethicone. Also, one kind or two or more kinds thereof may be used.

The total amount of the component (C) and the component (E) to be blended is from 50 to 95% by mass relative to the total mass of the cosmetic composition. The total amount is preferably from 60 to 90% by mass. When the amount is less than 50% by mass, a feeling in use becomes worse, such as stickiness. Moreover, when the amount exceeds 95% by mass, viscosity cannot be imparted and thus the case is not preferred. Also, when the total amount of the component (C) and the component (E) is taken as 100 parts by mass, the amount of the component (C) is 30 parts by mass or more, preferably 40 parts by mass or more, more preferably 50 parts by mass or more. When the amount is less than 30 parts by mass, the desired structure-recovering property is not obtained and thus the case is not preferred.

The component (D) is water. In the cosmetic composition of the invention, viscosity is imparted by hydration of the EO chain of the component (A) or the EO chain of nonion of the component (B). The water is not particularly limited as long as it is generally used in cosmetics, quasi drugs, and pharmaceuticals. For example, purified water such as distilled water or ion-exchanged water, physiological saline, phosphate buffer aqueous solutions, and the like can be employed.

The water is blended in an amount of 0.01 to 10% by mass relative to the total mass of the cosmetic composition. The amount is preferably from 0.1 to 8% by mass, more preferably from 0.1 to 5% by mass. When the amount is less than 0.01% by mass, the desired structure-recovering property is not obtained. Moreover, when the amount exceeds 10% by mass, a decrease in viscosity with time is observed and thus the case is not preferred.

In the cosmetic composition of the invention, according to need, further, it is possible to blend various components commonly used in cosmetics, pharmaceuticals, and the like within the range where the effects of the invention are not impaired. Examples thereof include a moisturizer; a hydrocarbon; a higher alcohol; a higher fatty acid; a triglyceride, an ester oil, an animal or vegetable oil and fat, or a silicone other than the components (C) and (E); a vitamin; a UV absorber; a water-soluble polymer; an antioxidant; a cationic surfactant; an anionic surfactant; an amphoteric surfactant; a nonionic surfactant other than the component (B); a metal ion sequestrant; ethanol; a thicker; an antiseptic agent; a coloring matter; a pigment; a perfume; and the like.

Moreover, the form of the cosmetic composition of the invention is not particularly limited but an oily cosmetic composition such as a cleansing oil, a hair oil, or a massage oil is suitable.

EXAMPLES

The following will describe the present invention in further detail with reference to Examples but the invention should not be construed as being limited thereto.

Synthetic Examples of the component (A) according to the invention are shown. The hydroxyl value was measured in accordance with JIS K 1557 1.

Synthetic Examples

Synthetic Example 1

Polyoxybutylene (48 mol) Polyoxyethylene (88 mol) Pentaerythritol Ether (Compound 1)

Into an autoclave were charged 45 g of pentaerythritol, 50 g of toluene, and 8.0 g of potassium hydroxide. After the air in the autoclave was replaced by dry nitrogen, 1,292 g of ethylene oxide was added dropwise from a dropping apparatus at 110° C. with stirring, followed by stirring for 2 hours. Subsequently, 1,160 g of 1,2-butylene oxide was added dropwise at 110° C., followed by stirring for 2 hours. Thereafter, a reaction product was taken out of the autoclave and neutralized with hydrochloric acid to be a pH of 6 to 7. For removing toluene and water contained, a treatment under reduced pressure was performed at 115° C. for 1 hour and finally salts were removed by filtration to obtain 2,345 g of Compound 1. The hydroxyl value was 56.0 mgKOH/g after the reaction with ethylene oxide and 30.0 mgKOH/g after the reaction with 1,2-butylene oxide.

Synthetic Example 2

Polyoxybutylene (45 mol) Polyoxyethylene (75 mol) Glyceryl (Compound 2)

Into an autoclave were charged 31 g of glycerin and 5.0 g of potassium hydroxide. After the air in the autoclave was replaced by dry nitrogen, 1,100 g of ethylene oxide was added dropwise from a dropping apparatus at 140° C. with stirring, followed by stirring for 2 hours. Subsequently, 1,080 g of 1,2-butylene oxide was added dropwise at 140° C., followed by stirring for 2 hours. Thereafter, a reaction product was taken out of the autoclave and neutralized with hydrochloric acid to be a pH of 6 to 7. For removing water contained, a treatment under reduced pressure was performed at 100° C. for 1 hour and finally salts were removed by filtration to obtain 2,180 g of polyoxybutylene (45 mol) polyoxyethylene (75 mol) glyceryl ether. The hydroxyl value was 49.6 mgKOH/g after the reaction with ethylene oxide and 25.4 mgKOH/g after the reaction with 1,2-butylene oxide.

The present inventors synthesized polyalkylene glycol derivatives having compositions shown in the following Table 1 in accordance with the above Synthetic Examples 1 and 2. In Table 1, Compounds 1 to 5 are the component (A) of the invention and Compounds 6 to 10 are comparative control component (A').

TABLE 1

| Compound | Z (m) | AO (*1) | EO (a) | AO (k) | EO parts by mass |
|---|---|---|---|---|---|
| 1 | Pentaerythritol (4) | C4 | 22 | 12 | 52.8 |
| 2 | Glycerin (3) | C4 | 25 | 15 | 50.5 |
| 3 | Pentaerythritol (4) | C4 | 10 | 20 | 23.4 |
| 4 | Sorbitol (6) | C8 | 15 | 10 | 34.0 |
| 5 | Diglycerin (4) | C4 | 40 | 10 | 71.0 |
| 6 | Diglycerin (4) | C4 | 0 | 25 | 0 |
| 7 | Glycerin (3) | — | 20 | 0 | 100 |
| 8 | Trehalose (8) | C4 | 40 | 10 | 71.0 |
| 9 | Diethylene glycol (2) | C4 | 45 | 40 | 40.7 |
| 10 | Pentaerythritol (4) | C3 | 22 | 12 | 58.2 |

(*1) C3 represents a 1,2-oxypropylene group, C4 represents a 1,2-oxybutylene group, and C8 represents a 1,2-oxyoctylene group Examples 1 to 12, Comparative Examples 1 to 5

Cosmetic compositions were prepared with the components and compositions shown in Table 2 and were evaluated for the structure-recovering property, transparency, smoothness when applied to the skin, and fitness with the skin.
<Preparation Method>
After the component (A), the component (B) or (B'), the component (C), and the component (E) were homogeneously dissolved at 70° C., the component (D) was gradually added and the whole was cooled to 25° C. with stirring.
<Evaluation Method>
Structure-Recovering Property:
At 25° C., shear viscosity (Pa·s) against shear velocity ($s^{-1}$) was measured twice. In this regard, a measuring interval was made 1 minute. A measuring instrument is as follows.
Measuring instrument: PaarPhysica MCR-300
Measuring tool: CP 50-2
After it was confirmed that the shear viscosity decreased against the shear velocity at both of the first time and the second time, the structure-recovering property was judged using a recovering ratio of the shear viscosity at a shear velocity of 0.1 ($s^{-1}$) as an index. "○" was regarded as qualified.
○: Structure-recovering property is observed.
Shear viscosity is recovered by 90% or more at the second time as compared with the case of the first time.
Δ: Poor structure-recovering property is observed.
Shear viscosity is recovered by 70% or more at the second time as compared with the case of the first time.
x: No structure-recovering property is observed.
Shear viscosity is recovered by 50% or less at the second time as compared with the case of the first time.
Transparency:
Appearance was visually confirmed at 25° C.
○: The composition is transparent.
Δ: Fluorescent color is observed.
x: The composition is turbid or white crystals are precipitated.
Smoothness when Applied
The oily cosmetic composition immediately after preparation was applied to an inner part of the forearm of 20 specialized female panelists under an environment of 25° C. and relative humidity of 50%. Evaluation was performed for the smoothness when applied based on the following criteria. An average point of 3.5 or more was regarded as a qualifying criterion.
5: Spreadability is very good and an extremely light feeling is exhibited.
4: Spreadability is good and a light feeling is exhibited.
3: Spreadability is slightly poor and a slightly scratchy feeling is exhibited.
2: Spreadability is bad and a heavy feeling is exhibited.
1: Spreadability is very bad and a sticky feeling is exhibited.
Fitness with the Skin
Following the evaluation for the smoothness when applied, the composition was evaluated for fitness with the skin after the passage of 1 hour under an environment of 25° C. and relative humidity of 50% based on the following criteria. An average point of 3.5 or more was regarded as a qualifying criterion.
5: A film feeling is good and a feeling of softening the skin is exhibited.
4: An appropriate film feeling is observed and a feeling of softening the skin is exhibited.
3: A film feeling is slightly strong but a feeling of softening the skin is exhibited.
2: A film feeling is slightly strong and a feeling of slightly softening the skin is exhibited.
1: A film feeling was strong and a feeling of stiffened skin is exhibited.
Evaluation results thereof are also collectively shown in Table 2.

TABLE 2

| | Component | HLB | Lipophilic group | Example (% by mass) 1 | 2 | 3 | 4 | 5 | 6 | 7 | 8 | 9 |
|---|---|---|---|---|---|---|---|---|---|---|---|---|
| A | Compound 1 | | | 10.0 | 10.0 | 10.0 | | | 10.0 | 10.0 | 10.0 | 20.0 |
| | Compound 5 | | | | | | 10.0 | 10.0 | | | | |
| B | POE(5 mol) oleyl ether | 9.0 | Oleyl group | 5.0 | | | | | | | | |
| | POE(10 mol) oleyl ether | 12.4 | Oleyl group | | 5.0 | | | | | | | |
| | POE(14 mol) diisostearate | 10.3 | Isostearyl group | | | 5.0 | | | | | | 5.0 |
| | POE(9 mol) monoisostearate | 11.6 | Isostearyl group | | | | 5.0 | | | | | |
| | POE(4 mol) monolaurate | 9.9 | Lauryl group | | | | | 5.0 | | | | |
| | POE(30 mol) tetraoleate | 11.2 | Oleyl group | | | | | | 5.0 | 5.0 | | |
| | POE(20 mol) glycerin triisostearate | 11.1 | Isostearyl group | | | | | | | | 5.0 | |

TABLE 2-continued

| | | | Lipophilic | | | | | | | | |
|---|---|---|---|---|---|---|---|---|---|---|---|
| B' | POE(20 mol) oleyl ether | 15.1 | Oleyl group | | | | | | | | |
| | POE(9 mol) dicaprate | 11.2 | Capryl group | | | | | | | | |
| | POE(20 mol) sorbitan monooleate | 15.7 | Oleyl group | | | | | | | | |
| C | 2-Ethylhexyl palmitate | | | | | | | 82.0 | 82.0 | 82.0 | 82.0 |
| | Glyceryl tri(2-ethylhexanoate) | | | 82.0 | 82.0 | 82.3 | | | | | 27.0 |
| | Isononyl isononanoate | | | | | | | | | | | 42.0 |
| | Pentaerythritol tetraoctanoate | | | | | | | | | | | |
| E | Cyclomethicone | | | | | | | | | | | 30.0 |
| | Liquid paraffin | | | | | | | | | | 55.0 | |
| D | Water | | | 3.0 | 3.0 | 2.7 | 3.0 | 3.0 | 3.0 | 3.0 | 3.0 | 3.0 |
| (A)/(B) or (A)/(B') mass ratio | | | | 2.0 | 2.0 | 2.0 | 2.0 | 2.0 | 2.0 | 2.0 | 2.0 | 4.0 |
| Parts by mass of component (C) in 100 parts by weight of all oily agents | | | | 100 | 100 | 100 | 100 | 100 | 100 | 100 | 32.9 | 58.3 |
| Structure-recovering property | | | | ○ | ○ | ○ | ○ | ○ | ○ | ○ | ○ | ○ |
| Transparency | | | | ○ | ○ | ○ | ○ | ○ | ○ | ○ | ○ | ○ |
| Smoothness when applied | | | | 3.8 | 3.7 | 4.2 | 4.0 | 3.8 | 4.1 | 4.2 | 4.3 | 4.5 |
| Fitness with skin | | | | 3.9 | 3.8 | 4.1 | 3.9 | 3.7 | 4.0 | 4.1 | 4.2 | 4.2 |

| | | | Lipophilic | Example (% by mass) | | | Comparative Example (% by mass) | | | | |
|---|---|---|---|---|---|---|---|---|---|---|---|
| | Component | HLB | group | 10 | 11 | 12 | 1 | 2 | 3 | 4 | 5 |
| A | Compound 1 | | | 5.0 | 3.0 | 7.2 | 10.0 | 10.0 | 10.0 | 10.0 | 18.0 |
| | Compound 5 | | | | | | | | | | |
| B | POE(5 mol) oleyl ether | 9.0 | Oleyl group | | 5.0 | | | | | | 3.0 |
| | POE(10 mol) oleyl ether | 12.4 | Oleyl group | | | | | | | | |
| | POE(14 mol) diisostearate | 10.3 | Isostearyl group | | 3.0 | | | | | 5.0 | |
| | POE(9 mol) monoisostearate | 11.6 | Isostearyl group | | | | | | | | |
| | POE(4 mol) monolaurate | 9.9 | Lauryl group | | | | | | | | |
| | POE(30 mol) tetraoleate | 11.2 | Oleyl group | 5.0 | 3.0 | | | | | | |
| | POE(20 mol) glycerin triisostearate | 11.1 | Isostearyl group | | | | | | | | |
| B' | POE(20 mol) oleyl ether | 15.1 | Oleyl group | | | | 5.0 | | | | |
| | POE(9 mol) dicaprate | 11.2 | Capryl group | | | | | 5.0 | | | |
| | POE(20 mol) sorbitan monooleate | 15.7 | Oleyl group | | | | | | 5.0 | | |
| C | 2-Ethylhexyl palmitate | | | | | | | | | | |
| | Glyceryl tri(2-ethylhexanoate) | | | 82.0 | 82.0 | | 82.0 | 82.0 | 82.0 | | 82.0 |
| | Isononyl isononanoate | | | | | | | | | | |
| | Pentaerythritol tetraoctanoate | | | | | 85.0 | | | | | |
| E | Cyclomethicone | | | | | | | | | | |
| | Liquid paraffin | | | | | | | | | | |
| D | Water | | | 3.0 | 3.0 | 2.8 | 3.0 | 3.0 | 3.0 | 3.0 | 3.0 |
| (A)/(B) or (A)/(B') mass ratio | | | | 1.0 | 0.5 | 1.4 | 2.0 | 2.0 | 2.0 | 2.0 | 6.0 |
| Parts by mass of component (C) in 100 parts by weight of all oily agents | | | | 100 | 100 | 100 | 100 | 100 | 100 | 0.0 | 100 |
| Structure-recovering property | | | | ○ | ○ | ○ | Δ | X | Δ | X | X |
| Transparency | | | | ○ | ○ | ○ | X | X | X | X | ○ |
| Smoothness when applied | | | | 3.8 | 3.7 | 3.8 | 3.4 | 3.3 | 2.9 | 2.1 | 3.5 |
| Fitness with skin | | | | 3.7 | 3.6 | 3.9 | 3.3 | 3.2 | 2.6 | 2.1 | 3.6 |

Examples 13 to 17, Comparative Examples 6 to 12

Cosmetic compositions were prepared with the components and compositions shown in Table 3 and were evaluated for the structure-recovering property, transparency, smoothness when applied to the skin, and fitness with the skin.

<Preparation Method>

After the component (A) or (A'), the component (B), the component (C), and the component (E) were homogeneously dissolved at 70° C., the component (D) was gradually added and the whole was cooled to 25° C. with stirring.

<Evaluation Method>

Structure-Recovering Property:

Similarly to Examples 1 to 12, the cosmetic compositions were evaluated for the structure-recovering property, transparency, smoothness when applied to the skin, and fitness with the skin.

Evaluation results thereof are collectively shown in Table 3.

TABLE 3

| | Component | Ex. 13 | Ex. 14 | Ex. 15 | Ex. 16 | Ex. 17 | Comp. 6 | Comp. 7 | Comp. 8 | Comp. 9 | Comp. 10 | Comp. 11 | Comp. 12 |
|---|---|---|---|---|---|---|---|---|---|---|---|---|---|
| A | Compound 1 | 10.0 | | | | | | | | | | | |
| | Compound 2 | | 10.0 | | | | | | | | | | |
| | Compound 3 | | | 10.0 | | | | | | | | | |
| | Compound 4 | | | | 10.0 | | | | | | | | |
| | Compound 5 | | | | | 10.0 | | | | | | | |
| A' | Compound 6 | | | | | | 10.0 | | | | | | |
| | Compound 7 | | | | | | | 10.0 | | | | | |
| | Compound 8 | | | | | | | | 10.0 | | | | |
| | Compound 9 | | | | | | | | | 10.0 | | | |
| | Compound 10 | | | | | | | | | | 10.0 | | |
| | Dextrin palmitate (*2) | | | | | | | | | | | 3.0 | |
| | N-Lauroyl-L-glutamic dibutylamide (*3) | | | | | | | | | | | | 0.5 |
| B | POE(30 mol) sorbitol tetraoleate HLB = 11.2 oleyl group | 5.0 | 5.0 | 5.0 | 5.0 | 5.0 | 5.0 | 5.0 | 5.0 | 5.0 | 5.0 | 5.0 | 5.0 |
| C | Glyceryl tri(2-ethylhexanoate) | 82.0 | 82.0 | 82.0 | 82.0 | 82.0 | 82.0 | 82.0 | 82.0 | 82.0 | 82.0 | 91.0 | 93.5 |
| D | Water | 3.0 | 3.0 | 3.0 | 3.0 | 3.0 | 3.0 | 3.0 | 3.0 | 3.0 | 3.0 | 1.0 | 1.0 |
| | (A)/(B) or (A)/(B') mass ratio | 2.0 | 2.0 | 2.0 | 2.0 | 2.0 | 2.0 | 2.0 | 2.0 | 2.0 | 2.0 | 2.0 | 2.0 |
| | Structure-recovering property | ○ | ○ | ○ | ○ | ○ | X | X | ○ | ○ | X | X | X |
| | Transparency | ○ | ○ | ○ | ○ | ○ | X | X | X | ○ | X | X | X |
| | Smoothness when applied | 4.1 | 3.8 | 3.9 | 3.8 | 3.6 | 2.3 | 1.8 | 3.4 | 3.3 | 2.1 | 3.2 | 3.1 |
| | Fitness with skin | 4.2 | 4.0 | 4.3 | 4.0 | 3.7 | 3.6 | 1.7 | 3.6 | 3.2 | 2.3 | 2.1 | 2.4 |

(*2) Rheopearl KL2 manufactured by Chiba Flour Milling Co., Ltd.
(*3) GP-1 manufactured by Ajinomoto Co., Inc.

Figure 2:
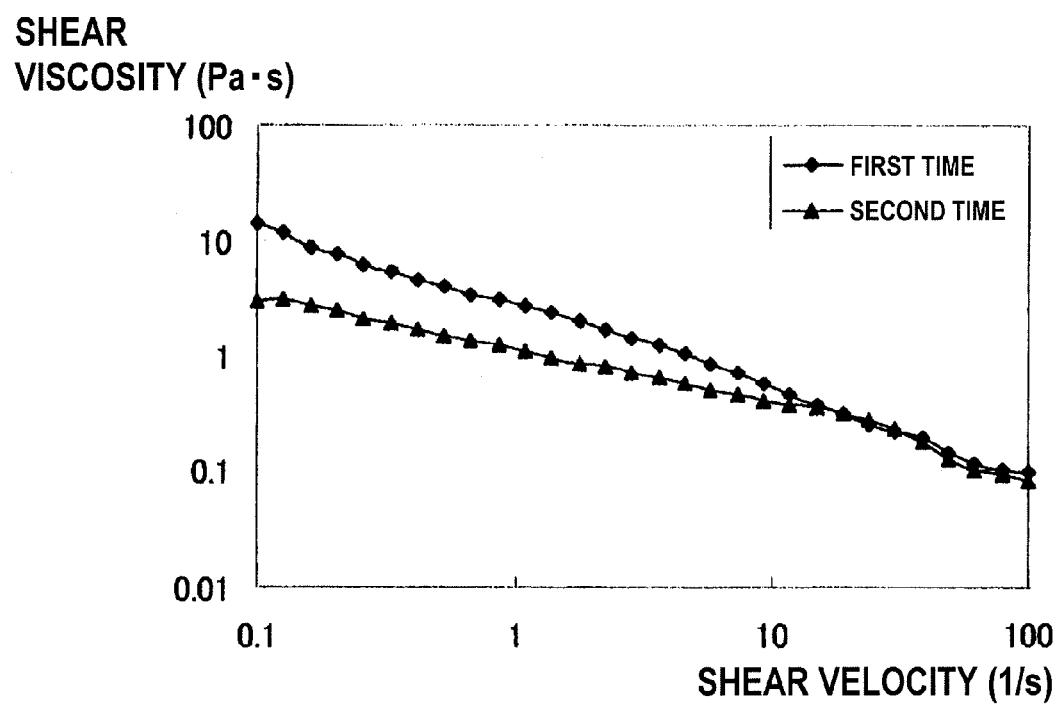
FIG. 2 is a drawing showing a relationship between shear velocity and shear viscosity of the cosmetic composition of Comparative Example 11.

Behavior of the shear viscosity against the shear velocity for Example 13 (structure-recovering property: ○, recovering ratio: 106%) and Comparative Example 11 (structure-recovering property: x, recovering ratio: 20%) are shown in FIG. 1 and FIG. 2, respectively.

The following will exemplify referential formulation of the cosmetic composition of the invention. In all Formulation Examples, "structure-recovering property", "transparency", "smoothness when applied", and "fitness with the skin" were good.

Formulation Example 1

Hair Oil

| | |
|---|---|
| (A) Compound 1 | 15.0% by mass |
| (B) POE (12 mol) dioleate (HLB 10.0) | 7.0% by mass |
| (B) POE (20 mol) glycerin triisostearate (HLB 10.4) | 5.0% by mass |
| (C) Glyceride of tri(caprylate/caprate) | 20.0% by mass |
| (C) Isononanyl isononanate | 10.0% by mass |
| (C) Olive oil | 5.0% by mass |
| (C) Camellia oil | 3.0% by mass |
| (E) Hydrogenated polyisobutene | 20.0% by mass |
| (E) Cyclomechicone | 10.0% by mass |
| (D) Water | 3.5% by mass |
| Vitamin E acetate | 0.2% by mass |
| Polyoxyethylene (10 mol) methylglucoside | 0.5% by mass |
| Glycerin | 0.2% by mass |
| Antiseptic agent | proper quantity |
| Perfume | proper quantity |

<Preparation Method>

After the components other than the component (D) were homogeneously dissolved at 70° C., the component (D) was gradually added and the whole was cooled to 25° C. with stirring.

Formulation Example 2

Massage Oil

| | |
|---|---|
| (A) Compound 1 | 5.0% by mass |
| (A) Compound 5 | 10.0% by mass |
| (B) POE (8 mol) monoisostearate (HLB 11.6) | 3.0% by mass |
| (B) POE (8 mol) glycerin monoisostearate (HLB 12.0) | 2.0% by mass |
| (C) Isopropyl palmitate | 15.0% by mass |
| (C) Ethyl oleate | 10.0% by mass |
| (C) Safflower oil | 15.0% by mass |
| (C) Castor oil | 3.0% by mass |
| (E) Liquid paraffin | 15.0% by mass |
| (E) Squalane | 15.0% by mass |
| (D) Water | 3.5% by mass |
| Dipropylene glycol | 1.0% by mass |
| 1,2-Octylene glycol | 0.5% by mass |
| Vitamin E | 0.5% by mass |
| Antiseptic agent | proper quantity |
| Perfume | proper quantity |

<Preparation Method>

After the components other than the component (D) were homogeneously dissolved at 70° C., the component (D) was gradually added and the whole was cooled to 25° C. with stirring.

Formulation Example 3

Cleansing Oil

| | |
|---|---|
| (A) Compound 1 | 10.0% by mass |
| (B) POE (30 mol) tetraisostearate (HLB 11.1) | 13.0% by mass |
| (B) POE (6 mol) sorbitan monooleate (HLB 11.8) | 3.0% by mass |
| (C) 2-Ethylhexyl palmitate | 20.0% by mass |
| (C) Glyceride of tri(2-ethylhexanoate) | 20.0% by mass |
| (C) Safflower oil | 15.0% by mass |
| (E) Hydrogenated polyisobutene | 15.0% by mass |
| (D) Water | 3.0% by mass |
| 1,3-Butylene glycol | 0.2% by mass |

-continued

| 1,2-Hexylene glycol | 0.2% by mass |
| Vitamin E | 0.3% by mass |
| Antiseptic agent | proper quantity |
| Perfume | proper quantity |

<Preparation Method>

After the components other than the component (D) were homogeneously dissolved at 70° C., the component (D) was gradually added and the whole was cooled to 25° C. with stirring.

While the invention has been described in detail and with reference to specific embodiments thereof, it will be apparent to one skilled in the art that various changes and modifications can be made therein without departing from the spirit and scope thereof.

The present application is based on Japanese Patent Application No. 2011-152689 filed on Jul. 11, 2011, and the contents are incorporated herein by reference. Also, all the references cited herein are incorporated as a whole.

The invention claimed is:

1. A cosmetic composition comprising the following components (A) to (D) at the following ratio based on the total cosmetic composition, wherein the component (A) is from 0.1 to 30% by mass, the component (B) is from 0.1 to 50% by mass, the component (C) is from 50 to 95% by mass, and the component (D) is from 0.01 to 10% by mass, and a mass ratio of the component (A) to the component (B), (A)/(B) is from 1/5 to 5/1:

(A) a polyalkylene glycol derivative represented by the following formula (I):

$$Z-\{O-(EO)_a-(AO)_k-H\}_m \quad (I)$$

wherein Z is a residual group resulting from removal of hydroxyl groups from a polyhydric alcohol having 3 to 6 hydroxyl groups, m is from 3 to 6, EO is an oxyethylene group, AO is an oxyalkylene group having 4 to 8 carbon atoms, and EO and AO are bonded in a block form; a represents an average molar number of EO added and k represents an average molar number of AO added, and a is from 1 to 50 and k is from 1 to 50; and a mass ratio of EO is from 10 to 75 parts by mass relative to 100 parts by mass of a total amount of EO and AO, (B) a nonionic surfactant having a polyoxyethylene group and a hydrocarbon group having 12 to 22 carbon atoms and exhibiting an Hydrophile-Lipophile Balance (HLB) of 8 to 14, (C) one or two or more oily agents selected from the group consisting of ester oils and triglycerides which are liquid at 25° C., and (D) water.

2. The cosmetic composition according to claim 1, wherein component (C) further comprises the following component (E) and wherein a part of the component (C) is replaced by said component (E) and an amount of the component (C) is 30 parts by mass or more relative to 100 parts by mass of a total amount of the component (C) and the component (E):

(E) one or two or more oily agents selected from the group consisting of hydrocarbon oils and silicone oils which are liquid at 25° C.

3. The cosmetic composition according to claim 1, wherein AO is a 1,2-oxybutylene group.

4. The cosmetic composition according to claim 1, wherein the component (B) is a nonionic surfactant having a branched or unsaturated hydrocarbon group having 12 to 22 carbon atoms.

5. The cosmetic composition according to claim 2, wherein AO is a 1,2-oxybutylene group.

6. The cosmetic composition according to claim 2, wherein the component (B) is a nonionic surfactant having a branched or unsaturated hydrocarbon group having 12 to 22 carbon atoms.

7. The cosmetic composition according to claim 3, wherein the component (B) is a nonionic surfactant having a branched or unsaturated hydrocarbon group having 12 to 22 carbon atoms.

8. The cosmetic composition according to claim 5, wherein the component (B) is a nonionic surfactant having a branched or unsaturated hydrocarbon group having 12 to 22 carbon atoms.

* * * * *